(12) United States Patent
Hochrein et al.

(10) Patent No.: US 8,446,656 B2
(45) Date of Patent: May 21, 2013

(54) METHOD FOR GENERATING TWO OPTICAL PULSES WITH A VARIABLE, TIME PULSE INTERVAL

(75) Inventors: Thomas Eugen Hochrein, Hettstadt (DE); Martin Koch, Kirchhain (DE); Norman Krumbholz, Trappenbeck (DE)

(73) Assignee: Menlo Systems GmbH, Martinsried (DE)

( * ) Notice: Subject to any disclaimer, the term of this patent is extended or adjusted under 35 U.S.C. 154(b) by 74 days.

(21) Appl. No.: 12/995,523

(22) PCT Filed: May 14, 2009

(86) PCT No.: PCT/DE2009/000662
§ 371 (c)(1),
(2), (4) Date: Jan. 26, 2011

(87) PCT Pub. No.: WO2009/146671
PCT Pub. Date: Dec. 10, 2009

(65) Prior Publication Data
US 2011/0141540 A1 Jun. 16, 2011

(30) Foreign Application Priority Data
Jun. 3, 2008 (DE) .......................... 10 2008 026 484

(51) Int. Cl.
*G02B 26/00* (2006.01)
*G01J 3/00* (2006.01)
(52) U.S. Cl.
USPC ......................................... 359/238; 356/300
(58) Field of Classification Search
USPC .................... 359/238, 349, 359, 237; 372/25, 372/30, 700; 356/300–303, 326–327, 316, 356/450–451, 323, 331, 317
See application file for complete search history.

(56) References Cited

U.S. PATENT DOCUMENTS

| 4,039,851 | A |   | 8/1977 | Jain et al. |        |
|-----------|---|---|--------|-------------|--------|
| 4,639,075 | A | * | 1/1987 | Salour et al. | 385/31 |

(Continued)

FOREIGN PATENT DOCUMENTS

| DE | 102005011045 A1 | 11/2006 |
|----|-----------------|---------|
| EP | 12 81 061 B1    | 2/2003  |

(Continued)

OTHER PUBLICATIONS

Bartels A et al., "Ultrafast time-domain spectroscopy based on high-speed asynchronous optical sampling", Review of Scientific Instruments, American Institute of Physics, Mar. 22, 2007, pp. 35107-35107, XP012103859, ISSN: 0034-6748, Melville, New York, U.S.

(Continued)

*Primary Examiner* — Ricky Mack
*Assistant Examiner* — Tuyen Tra
(74) *Attorney, Agent, or Firm* — McGlew and Tuttle, P.C.

(57) ABSTRACT

A method for generating two delayed pulses, in particular in terahertz spectroscopy and/or in pump-probe experiments, with the following method steps:
 generating a pulsed beam using a beam source, in particular a pulsed laser;
 dividing the pulsed beam, where a first partial beam contains a first pulse and a second partial beam contains a second pulse;
 directing the two pulses onto a respective target area, the first pulse directly reaching a first target area and the second pulse reaches a second target area after covering a delay path, and the two target areas may coincide;
 using the two pulses, in particular for a measuring method, where a time delay of the two pulses in the respective target area is adjustable by a pulse repetition rate of the pulsed beam.

23 Claims, 4 Drawing Sheets

U.S. PATENT DOCUMENTS

| | | | |
|---|---|---|---|
| 5,315,604 A * | 5/1994 | Chiu et al. | 372/25 |
| 6,320,191 B1 | 11/2001 | Rudd | |
| 6,373,867 B1 * | 4/2002 | Lin et al. | 372/18 |
| 2001/0045513 A1 | 11/2001 | Kourogi et al. | |
| 2005/0073689 A1 | 4/2005 | Pang et al. | |
| 2006/0285853 A1 * | 12/2006 | Murai | 398/152 |

FOREIGN PATENT DOCUMENTS

| | | |
|---|---|---|
| JP | 2001-227911 A | 8/2001 |
| JP | 2004-349582 A | 12/2004 |
| JP | 2007-248100 A | 9/2007 |
| WO | WO 2007/079342 A | 7/2007 |

OTHER PUBLICATIONS

Vieweg, N et al., Fiber-coupled THz spectroscopy for monitoring polymeric compounding processes, In: Proc. SPIE, vol. 6616, 66163M-1 to 66163M-8, 2007.

* cited by examiner
METHOD FOR GENERATING TWO OPTICAL PULSES WITH A VARIABLE, TIME PULSE INTERVAL

CROSS REFERENCE TO RELATED APPLICATIONS

This application is a United States National Phase application of International Application PCT/DE2009/000662 and claims the benefit of priority under 35 U.S.C. §119 of German patent application DE 10 2008 026 484.9 filed Jun. 3, 2008, the entire contents of which are incorporated herein by reference.

FIELD OF THE INVENTION

The present invention relates to a method for generating two delayed pulses, in which a time delay can be achieved without the use of mechanical parts and in which, in particular, the time delay can be varied in particular in terahertz spectroscopy and/or in pump-probe experiments, with the following method steps:
  generating a pulsed beam using a beam source, in particular a pulsed laser;
  dividing the pulsed beam, wherein a first partial beam contains a first pulse and a second partial beam contains a second pulse;
  directing the two pulses onto a respective target area, wherein the first pulse directly reaches a first target area and the second pulse reaches a second target area after covering a delay path, and wherein the two target areas may coincide;
  using the two pulses, in particular for a measuring method.

BACKGROUND OF THE INVENTION

It is known to use a femtosecond laser in a method in order to activate, using the optical pulses thereof, a photoconductive dipole antenna. In the dipole antenna the laser pulses generate free charge carriers, which are accelerated by an external electrical field. The accelerated charge carriers, in the form of a short current pulse, form the source for an electromagnetic pulse radiated into the space. The electromagnetic pulses generated in this manner may, for example, be used for investigating material, these being used in turn, for example, for monitoring during the production processes of plastics material products or to analyze material. The generation of two time delayed pulses is also the basis for further fields of application such as pump-probe methods, optical tomography, interferometric measurements etc.

These methods are most widespread in the form where a pulsed beam is generated using a beam source, in particular a laser. This beam is divided into a first partial beam with a first pulse and a second partial beam with a second pulse and the pulses are then directed into a target. In this case, one of the two pulses covers a path which is different from the second pulse. This delay path can be realized in the most varied ways, such as, for example, by a mirror, which opposes a second mirror, the spacing of the two mirrors being controllable by means of a precise mechanism or an electronic system. An injected, pulsed beam, in a structure of this type, can cover an adjustable path, which is called a delay path. This path is used to adjust the time delay from a pulse decoupled before this delay path. In this case, a main problem consists in permanently adjusting the mechanical arrangement of the delay path and it is known from constructional systems in this regard that they frequently have to be readjusted.

It is furthermore known from the prior art to configure a delay path for optical signals with a decoupling mirror, which has a spirally curved mirror face. DE 10 2005 011 045 A1 in this regard shows a mirror face with a spiral curvature, the radius changing with the change in the angle of rotation. If a mirror of this type is installed in a corresponding arrangement, the delay path can be changed by rotating the mirror. The mirror body, for this purpose, has two mirror faces, which are arranged symmetrically with respect to a center point, each partial face, starting with an increasing radius, running from a minimum radius through to a maximum radius. Similar problems are produced here as in the previously mentioned prior art in that a mechanism, in this case a rotary mechanism, is required to adjust the delay path, which has to be very precise, and in that the delay path is limited with regard to its variability depending on the radius.

In the conventional method, in particular in the method described above to generate time delayed pulses, the time delay is coupled to the length of the delay path. A limitation of the time delay is thereby produced in that the length of the delay path is limited by the size of the structure. Because of the mechanisms used and the component geometries used, the variability of the delay paths in constructional systems of this type is also very limited. With regard to the delay paths used, problems are also produced with regard to the readjustment and imprecisions due to vibrations at the structure, as with longer optical path lengths covered, the lateral deviations in the sense of the beam laws increase proportionally thereto.

SUMMARY OF THE INVENTION

Proceeding from this prior art, the object of the present invention is to provide a method for generating delayed pulses, with which the drawbacks to be found in the prior art can be overcome and, in particular, a simplified adjustment is made possible.

This object is achieved according to the invention by a method in which a time delay of the two pulses in the respective target area is adjustable by means of a pulse repetition rate of the pulsed beam.

The method of the invention thus basically comprises the following disclosed method steps:
  generating a pulsed beam using a beam source, in particular a pulsed laser, which generates a pulsed signal in the form of repeated pulses, for example with a duration in the range of femtoseconds. However, in this case, a laser pulse can also easily be used on another timescale and practically at each repetition frequency, other types of beams, such as, for example, electromagnetic pulses also being able to be used to apply the proposed method, for example, to generate time delayed pulses in microwave technology.
  dividing the pulsed beam, in which the first partial beam contains a first pulse and the second partial beam contains a second pulse. For this purpose, a beam splitter can be used which allows the various fractions with the same or different intensities through, such as, for example, a partially permeable mirror for a structure, in which the laser beam is freely arranged. In addition it is provided, in one structure, in which light guides, such as, for example, glass fiber cables, are used, to provide a fiber coupler as a beam splitter. Thus, the signal can be guided in the light guide and divided, without carrying out readjustments on the structure of a system of this type. In principle, all elements can be used, even from other areas of technology, which allow a division of a signal into two fractions.

directing the two pulses to a respective target area, the first pulse directly reaching a first target area and the second pulse reaching a second target area after covering a delay path. It is also provided for this purpose that the two target areas may coincide. Substantially fixed paths which the signal beam covers are thought of here, it being possible to adapt these to the method if necessary. Above all, with regard to the adjustment of a system, the variability thereof is provided. It should be particularly emphasized that the two partial beams have to cover different path lengths in order to arrive at a time delay as described in the following manner.

using the two pulses, the two pulses observed in this case being selectively taken from the pulsed signal and directed into a respective target area. These pulses are finally available for further purposes, such as, for example, for applications in terahertz technology. In this case, they reach dipole antennae and generate free charge carriers, which are accelerated in an applied outer electrical field and emit a terahertz pulse. When target areas coincide, the use of this method for optical measurements from ultra-short time physics is to be thought of, for example, in which the pulses originate from the same pulse of the pulsed source and are overlaid in a target area. To measure the pulses, for example, the pulse form is indicated from the overlaying of the pulse with itself by cross correlation. The directing of the two pulses can be carried out here free of the geometric configuration of the structure, in particular as a free beam or as a closed fiber-guided system.

According to the invention, the time delay of the two pulses in the respective target area can be adjusted by means of the pulse repetition rate of the pulsed beam and variably changed. With substantially fixed optical path lengths, which the first pulse and the second pulse cover, a change in the interval of the two pulses is produced in the respective target area and, in particular, a variation in the time delay of the two pulses in the respective target area owing to a change in the repetition rate. It is also possible in this manner to adjust the interval of the two pulses or the time delay of the two pulses in the respective target area with the repetition rate.

Consequently, two or more pulses can be directed into a respective target area, it being possible on the basis of the proposed method to adjust the time interval between the impinging of the individual pulses in the respective target area by means of the repetition rate. There is no restriction of any type to the effect that the time delay is limited, for example, by a finite delay path. It is therefore now in particular possible in terahertz technology, to generate two terahertz pulses which have a very large time interval with respect to one another. Avoidance of the adjustment of moveable parts during the method facilitates the work in that it is substantially more seldom necessary to readjust the structure, a more precise operation afflicted by fewer errors of a device of this type being produced because of the reduction in number of moveable parts. The use of glass fiber cables for guiding the laser beam or the pulsed signal allows a very stable structure, it also being possible to achieve simpler assembly for products which relate to a structure for using a proposed method.

It is provided in a preferred embodiment that the pulsed beam impinges on a beam splitter, in particular on a fiber coupler and is divided into a first partial beam with a first pulse and a second partial beam with a second pulse. The beam splitter mentioned here may be configured as semi-permeable mirrors for a so-called free beam structure, a possibility also existing for generating a plurality of pulses by the use of a plurality of partially permeable beam splitters. In fiber-coupled systems, a fiber coupler is a possibility by way of example for the beam splitter in order to separate the pulsed beam into a first fiber, which contains a first partial beam with a first pulse, and into a second fiber, which contains a second partial beam with a second pulse, it being possible to carry this out with all types of light guides.

It is provided in a further configuration that the first and the second pulse come from the same pulse of the pulsed signal, a measurement of the pulse only being thought of by way of example. It may furthermore be provided that the first pulse and the second pulse originate from different pulses of the pulsed signal in order to achieve a time delay of the electromagnetic pulses generated during the production, for example, of electromagnetic pulses, which originate from activated dipole antennae. Thus, depending on the required time delay, a corresponding first and second pulse from the pulsed signal can be used. To use the pulses for pulse measurement, applications in the area of ultra-short time physics are thought of by way of example, in order to overlay femtosecond or attosecond pulses, for example, by means of cross correlation and to integrate them in a slow photodetector via the signal in order to come to conclusions about their form and to check the signal quality.

According to a further embodiment of the invention, the first pulse is directed by means for beam deflection into a target area. This may take place in a simple manner, for example by means of a mirror or in a free beam structure. Analogously to this, in a fiber-coupled system, a signal can be deflected by a correspondingly formed light guide. In order to adjust the beam deflection or adapt it to the use, further means for adjustment are thought of. Likewise, further optical components and/or means for beam deflection can also be inserted in a further use according to requirements.

According to a preferred embodiment, the second pulse is directed by means for beam deflection into a target area, it being provided that the pulse covers a path which is different from the first pulse, in particular a longer delay path. A delay path, in particular, means a longer path in comparison to the first pulse, in this case. These can be any means for beam deflection. Mirrors or glass fibers are preferably in turn used. The length of the delay path is implemented, by way of example, with a fixed length, which may be changed, however, for adjustment and also for continuing pulse generation. For precise calculation of the time delay or to adjust it, it may be necessary for the first and second pulse to cover a different path.

Moreover, it is particularly preferred for the delay path, which the second pulse covers to have a constant length, which is different from zero, in order to keep the time delay of the first and the second pulse substantially constant in the respective target area. Moreover, it is found that the time delay is variably adjustable in principle by means of the repetition rate. The delay path, which the second pulse covers, can likewise, in particular in terahertz spectroscopy, be realized by a longer glass fiber in comparison to the glass fiber, which guides the first pulse.

According to a particularly preferred configuration, the delay path is configured as an arrangement to compensate the pulse widening, by dispersion in a glass fiber or else in air. In this case, it is possible to also provide further optical elements in the delay path, which can change the pulse not only in relation to its form and duration.

In order to adjust the time delay of the two pulses in the respective target area by means of the repetition rate of the pulsed signal, it is particularly preferably provided that the length of the delay path be kept constant and only be adapted for adjustment. This produces a substantial improvement to constructional systems in this regard as the time delay is not carried out by means of the change in the length of the delay path and therefore the change in the delay path does not lead to errors, either.

According to a further configuration of the invention it may be provided that the time delay of the two pulses in the respective target is produced from the length of the delay path, the speed of propagation of the pulses, the pulse repetition rate and a factor for the number of pulses of the laser source, which lies between the pulses generating the first and the second pulse. In this case, the length of the delay path takes into account the length from the beam splitter to the first impingement point, the length from the beam splitter to a possibly present means for beam deflection and the length from a possibly present means for beam deflection to a second impingement point.

According to a most simple implementation of the structure with a respective light guide for the first and the second partial beam or pulse, only the length difference of the two light guides can be regarded as the delay path. In this embodiment, using the speed of propagation, the ratio of the refraction index and the vacuum light speed for the material has to be taken into account, through which the two signals are guided, wherein no limitation should be produced to the effect that different light guides are also used to guide the first and the second pulse. The factor for the number of pulses of the laser source, which lie between the pulses generating the first and the second pulse, is produced, in the simplest case, from a listed numbering of the pulses, which leave the pulsed beam source.

It may furthermore be provided that the repetition rate is determined by means of photo sensors and used to determine the time delay when the length of the delay path is known. Although the repetition rate can also be determined by means of the length of the resonator in the laser, it may, however, be more favorable to decouple the signal and to determine the repetition rate by means of a photo sensor. This may take place by means of any optical elements which are used to allocate an electrical signal to a light signal, the measurement of intensities then, by way of example, being reduced to a measurement of voltages.

According to a further preferred embodiment of the method according to the invention it may be provided that a variation of the time delay of the first and second pulse in the respective target area is achieved by means of varying the pulse repetition rate. Thus, for example, relaxation processes can be resolved with respect to time to thus come to conclusions about time-dependent processes within the subject investigated. Furthermore, it may additionally be provided that a corresponding investigation is repeatedly carried out under the same conditions with a rigidly adjusted repetition rate with a constant time interval of the two pulses, as a specific result can thus be determined more precisely. The concluding use of the two pulses in the respective target area is particularly preferably provided to generate and/or detect an electromagnetic pulse. This is to be attributed to a use in terahertz physics, a dipole antenna being exposed to a laser pulse and the generated free charge carriers in an electrical field being accelerated and thus generating a terahertz pulse. The application of the time-delayed pulses is very diverse in principle and can be used, in particular, to measure processes on very small timescales. In this case, it is now possible to carry out a continuous measurement of various states of a system which are in a time sequence, by means of the adjustment of the time delay in a large area.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
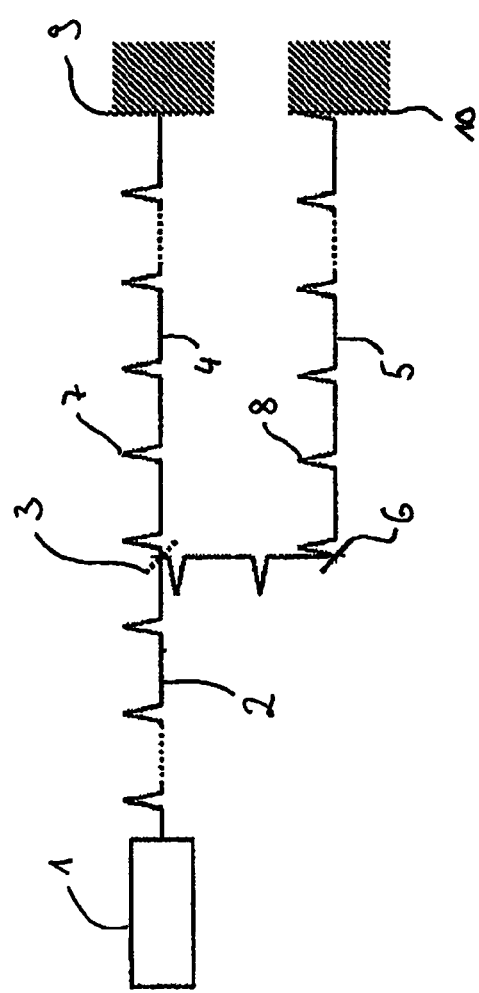
FIG. 1 is a schematic view of a system for using the method, the two pulses impinging in the respective target area with a slight time offset.

Referring to the drawings in particular, FIG. 1 shows an arrangement for carrying out the method according to the invention with a laser light source 1, which generates a pulsed beam 2, which impinges on a beam splitter 3 and is divided into a first partial beam 4 and a second partial beam 5. The second partial beam is deflected by means for beam deflection 6. The first partial beam 4 contains a first pulse 7, which is directed to a first target area 9. The second partial beam 5 contains a second pulse 8, which is directed to a second target area 10. The second partial beam 5 covers a delay path, which lies between the beam splitter 3 and the means for beam deflection 6. A pulse generated at a specific repetition rate is divided by a beam splitter 3, which may be configured here as a semi-permeable mirror, into a first pulse 7, which lies in a first partial beam 4, and into a second pulse 8, which lies in a second partial beam 5. In this case, the delay path is selected as a function of the repetition rate in such a way that the pulses from the first partial beam 4 and from the second partial beam 5 in each case impinge with a slight time offset in the respective target 9, 10. For this purpose, the delay path is freely selectable with respect to its length and corresponds here, for example, to approximately twice the pulse interval of the pulses leaving the pulsed laser. The interval of the two pulses, which originate from a pulse of the pulsed laser beam and are at the same level, is about two pulses. In this manner, a first pulse 7 arrives in a first target 9 when a second pulse 8 arrives in a second target 10 approximately simultaneously, this second pulse 8 originating from the pulse of the laser source which lies two pulses before the pulse which generates the first pulse. In this case, two pulses in each case arrive virtually synchronously in a respective target area and may, for example, activate a dipole antenna to synchronously generate an electromagnetic pulse, such as, for example, a terahertz pulse.

Figure 2:
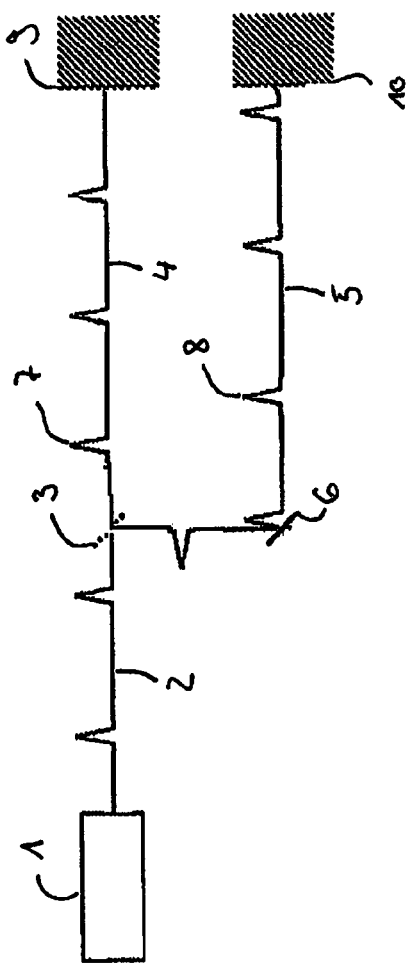
FIG. 2 is a schematic view of a system for using a proposed method for generating two pulses with a smaller repetition rate than in FIG. 1, the pulses impinging highly offset with respect to time in the respective target area.

FIG. 2 also shows an arrangement for carrying out a method according to the invention with a laser 1, from which a pulsed beam 2 impinges on a beam splitter 3 and is divided into a first partial beam 4 and a second partial beam 5. The first partial beam 4 contains a first pulse 7, which is directed into a first target 9. The second partial beam 5 covers a delay path, which lies between the beam splitter 3 and a means for beam deflection 6. The second pulse 8 from the second partial beam 5 is directed into a second target 10 after a delay path has been covered. The present figure is shown with a smaller repetition rate to make clear a situation in which the pulses do not impinge synchronously in their respective impingement point. In this case, the selection of the length of the delay path is basically free and determines the position of the pulses at a specific repetition rate. It is also important here for the length of the delay path to be fixed and basically independent of the method applied. If the pulses are indicated, by way of example, a first pulse and a second pulse can be identified by I, as the two pulses are allocated to the Ist pulse, which originates from the beam source. The number of pulses per path length is the same in the two partial beams and predetermined by the repetition rate. A change in the repetition rate produces a uniform displacement of the pulses in the first and second partial beam relative to one another. The total displacement of the pulses is proportional to the number of pulses in the respective partial beam and is produced from the sum of the individual displacements of the pulses with respect to one another. As the length of the two partial beams from the beam splitter to the respective impingement point is different, a different displacement of the pulses is produced in the target region, depending on the number of pulses which the respective partial beam contains. Accordingly, the total displacement in the shorter partial beam is smaller as this contains fewer pulses. In the reverse conclusion a greater displacement is produced for the longer partial beam with a larger number of pulses.

The calculation of the pulse delay by changing the repetition rate will be described below.

The time interval $\tau$ of two consecutive pulses of the laser with the repetition rate R corresponds to $\tau_0 = 1/R$ In general, the time interval $\tau$ of a pulse $I(i) = i$ from the pulse $I(i+a) = i+a$ with the pulse interval $\Delta I = I(i+a) - I(i) = a$ can be described as follows.

$$\tau = \Delta I \cdot \tau_0 = \Delta I / R$$

The running time t of an electromagnetic wave through a medium with the refraction index n and a path l passed through at the vacuum light speed $c_0$ is $$t = l \cdot n / c_0.$$

If the time difference $\Delta t$ of the impingement time of a pulse $I(i)$ is observed in the two partial beams, this is composed of the time required to cover the paths beam splitter-impingement point 1 at $t_1$, beam splitter-means for deflection of the beam at $t_v$ and means for deflecting the beam-impingement point 2 at $t_2$ and produces $$\Delta t = t_2 + t_v - t_1,$$

wherein this at $t_1$=constant and $t_2$=constant and $t_v$=variable corresponds to the conventional delay path.

Therefore the interval between the impingement time of a pulse $I(i) = i$ in the first partial beam and of a pulse $I(i+a) = i+a$ in the second partial beam at $\Delta I = a$ is $$\Delta \tau = t_2 + t_v - t_1 - \tau.$$

Therefore, for the second interval $$\Delta \tau = l_2 \cdot n_2 / c_0 + l_v \cdot n_v / c_0 + l_1 \cdot n_1 / c_0 - \Delta I / R.$$

is produced.

Therefore, taking into account all the paths and refraction indices while observing two different pulses, the pulse delay can be varied by changing the repetition rate.

In addition, the variation area of the pulse delay from the repetition rate may be varied between $R_{min}$ and $R_{max}$. This produces $$\Delta \tau_{var} = \Delta I \cdot (1/R_{min} - 1/R_{max})$$

Figure 3:
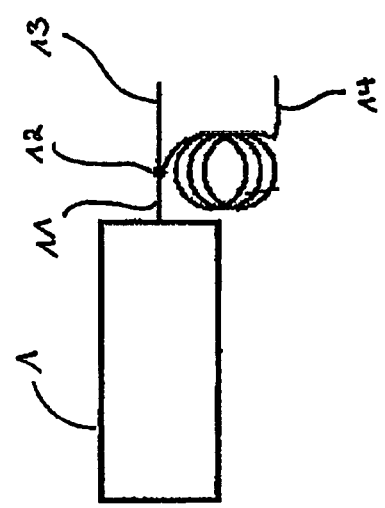
FIG. 3 is a schematic view of a fiber-coupled system.

FIG. 3 shows, by way of example, a closed system using light guides or glass fiber cables to carry out a method according to the invention, a laser 1 being coupled to a first light guide 11, which impinges on a fiber coupler 12 and is divided into two further light guides 13, 14. The second light guide 13 directly reaches a target, while the third light guide 14 reaches a second target after a delay path has been covered or a longer light path in the exemplary glass fiber cable. It can clearly be seen here how a fixed delay path is realized in a fiber-assisted structure of this type. One advantage of a device according to this example may be a possible transportable configuration or else a light construction of a device of this type to realize a method according to the invention.

Figure 4:
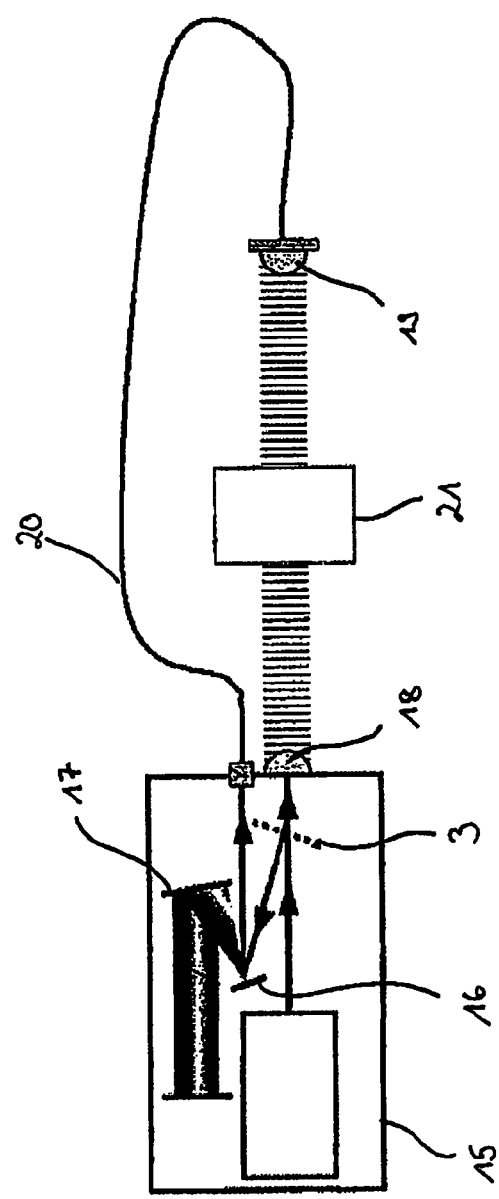
FIG. 4 is a schematic view of a system for generating terahertz pulses, with a device for pulse compensation.

FIG. 4 schematically shows a structure for generating terahertz pulses with a housing 15, a laser 1, which sends a pulsed beam to a beam splitter 3, a first partial beam being directed to a first dipole antenna 18 and a second partial beam being directed to a mirror 16, which supplies this partial beam to an arrangement for pulse compensation 17 and injects the second partial beam into a glass fiber 20, which directs the latter into a second dipole antenna 19. In this case, the first dipole antenna 18 generates a terahertz pulse, with which an object 21 to be investigated is irradiated. In the second dipole antenna 19, the transmitted terahertz pulse is scanned stepwise by varying the pulse delay by the laser pulse. The sample 21 in the middle can thus be investigated with terahertz pulses from the dipole antenna 18, which have a specific time delay until detection at the dipole antenna 19, it being possible to adjust this specific time delay by means of the repetition rate of the laser 1.

While specific embodiments of the invention have been described in detail to illustrate the application of the principles of the invention, it will be understood that the invention may be embodied otherwise without departing from such principles.

LIST OF REFERENCE NUMERALS

01 Laser
02 Pulsed beam
03 Beam splitter
04 First partial beam
05 Second partial beam
06 Means for beam deflection
07 First pulse
08 Second pulse
09 First target area
10 Second target area
11 First light guide
12 Fiber coupler
13 Second light guide
14 Third light guide
15 Housing
16 Mirror
17 Means for pulse compensation
18 First dipole antenna
19 Second dipole antenna
20 Glass fiber
21 Sample

The invention claimed is:
1. A method for generating two delayed pulses, the method comprising the following method steps:

generating a pulsed beam using a beam source;
dividing the pulsed beam, wherein a first partial beam contains a first pulse and a second partial beam contains a second pulse;
directing the two pulses onto a respective target area, wherein the first pulse directly reaches a first target area and the second pulse reaches a second target area after covering a delay path;
using the two pulses in one or more of a terahertz spectroscopy experiment and a pump-probe experiment, wherein a time delay of the two pulses in the respective target area is adjusted by means of a pulse repetition rate of the pulsed beam in said one or more of said terahertz spectroscopy experiment and said pump-probe experiment.

2. A method according to claim 1, wherein the pulsed beam impinges on a beam splitter and is divided into the first partial beam with the first pulse and the second partial beam with the second pulse.

3. A method according to claim 2, wherein the first pulse and the second pulse originate from one of the group of the same pulse and different pulses of the beam source.

4. A method according to claim 2, wherein the beam splitter is a fiber coupler.

5. A method according to claim 1, wherein the first pulse is directed into a target area by means for beam deflection, wherein a sample is excited by a terahertz pulse and a subsequent pulse tests a response of the sample after the sample is excited via said terahertz pulse in said one or more of terahertz spectroscopy and pump-probe experiments.

6. A method according to claim 1, wherein the second pulse is directed into a target area by means for beam deflection and, in the process, covers a path which is different from the first pulse, wherein radiation is applied in a terahertz range to a sample in said one or more of terahertz spectroscopy and pump-probe experiments.

7. A method according to claim 1, wherein the delay path, which the second pulse covers, has a constant length, which is different from zero.

8. A method according to claim 7, wherein the constant length of the delay path adapts to at least one of said one or more of said terahertz spectroscopy experiment and said pump-probe experiment and for adjustment.

9. A method according to claim 1, wherein the delay path is an arrangement to compensate the pulse widening.

10. A method according to claim 1, wherein the time delay of the two pulses in the target is produced from the length of the delay path, a speed of propagation of the pulses, the pulse repetition rate and a factor for the number of pulses of a laser source, said factor being between the pulses generating the first and the second pulse.

11. A method according to claim 1, wherein the repetition rate is determined and is used to determine the time delay when the length of the delay path is known.

12. A method according to claim 11, wherein a variation of the pulse repetition rate corresponds to a variation of the time delay of the first and second pulse.

13. A method according to claim 1, wherein the pulses are used in the target area to at least one of generate and detect an electromagnetic pulse.

14. A method according to claim 1, wherein the two pulses are used for a measuring method.

15. A method according to claim 1, wherein the beam source is a pulsed laser.

16. A method according to claim 1, wherein the two target areas coincide.

17. A method according to claim 1, wherein the first pulse is directed into a target area by at least one of mirrors and light guides.

18. A method according to claim 1, wherein the second pulse is directed into a target area by at least one of mirrors and light guides, and, in the process, covers a path which is different from the first pulse.

19. A method according to claim 1, wherein the second pulse is directed into a target area by means for beam deflection and, in the process, covers a longer delay path.

20. A method according to claim 1, wherein the second pulse is directed into a target area by at least one of mirrors and light guides, and, in the process, covers a longer delay path.

21. A method according to claim 1, wherein the delay path, which the second pulse covers, has a constant length, which is different from zero and said delay path is at least one of a free beam and a glass fiber.

22. A method according to claim 1, wherein the repetition rate is determinable by photo sensors.

23. A method for generating two delayed pulses, the method comprising the following method steps:
generating a pulsed beam using a beam source;
dividing the pulsed beam to form a first partial beam and a second partial beam, wherein said first partial beam comprises a first pulse and said second partial beam comprises a second pulse;
providing a first dipole antenna and a second dipole antenna, said first partial beam being directed to said first dipole antenna, said second partial beam being directed to said second dipole antenna, said second pulse reaching said second dipole antenna after covering a delay path;
generating a terahertz pulse based on said first partial beam;
irradiating a sample with said terahertz pulse;
detecting an electromagnetic pulse with said second dipole antenna after said sample is irradiated with said terahertz pulse, wherein a time delay of said first pulse and said second pulse is adjusted by means of an adjustable pulse repetition rate of the pulsed beam.

* * * * *